United States Patent
Robinson et al.

(10) Patent No.: US 11,455,747 B2
(45) Date of Patent: Sep. 27, 2022

(54) DIGITAL IMAGING SYSTEMS AND METHODS OF ANALYZING PIXEL DATA OF AN IMAGE OF A USER'S BODY FOR DETERMINING A USER-SPECIFIC SKIN REDNESS VALUE OF THE USER'S SKIN AFTER REMOVING HAIR

(71) Applicant: THE GILLETTE COMPANY LLC, Boston, MA (US)

(72) Inventors: Susan Clare Robinson, Windsor (GB); Leigh Knight, Reading (GB)

(73) Assignee: The Gillette Company LLC, Boston, MA (US)

( * ) Notice: Subject to any disclaimer, the term of this patent is extended or adjusted under 35 U.S.C. 154(b) by 312 days.

(21) Appl. No.: 16/919,230

(22) Filed: Jul. 2, 2020

(65) Prior Publication Data
US 2022/0005227 A1    Jan. 6, 2022

(51) Int. Cl.
*G06T 7/90* (2017.01)
*G16H 10/60* (2018.01)
(Continued)

(52) U.S. Cl.
CPC .............. *G06T 7/90* (2017.01); *G06T 7/0014* (2013.01); *G16H 10/60* (2018.01); *G16H 50/20* (2018.01);
(Continued)

(58) Field of Classification Search
CPC ................................ G16H 10/60; G16H 50/20
See application file for complete search history.

(56) References Cited

U.S. PATENT DOCUMENTS 5,252,331 A    10/1993   Curtis et al.
9,013,567 B2    4/2015   Clemann et al.
(Continued)

FOREIGN PATENT DOCUMENTS

EP        3651949 A1       5/2020
WO   WO-2011106792 A2    9/2011
WO   WO-2019136354 A1    7/2019

OTHER PUBLICATIONS

ScienceInsider: Youtube video "What Are Ingrown Hairs—And How To Treat Them", Published Jun. 2, 2018. https:// www.youtube.corn/watch?v=laevAwpnPjc <https://www.youtube.corn/watch?v=laevAwpnPjc> (Year: 2018).

*Primary Examiner* — Edward Park
(74) *Attorney, Agent, or Firm* — Kevin C. Johnson

(57) ABSTRACT

Digital imaging systems and methods are described for determining a user-specific skin redness value of a user's skin after removing hair. An example method may be performed by one or more processors and may include aggregating training images comprising pixel data of skin of individuals after removing hair. A skin redness model may be trained using the training images to output skin redness values associated with a degree of skin redness from least to most red. The method may include receiving an image of a user including pixel data of the user's skin after hair is removed from the skin, analyzing the image using the skin redness model to determine a user-specific skin redness value, generating a user-specific recommendation designed to address a feature identifiable within the pixel data of the user's skin, and rendering the recommendation on a display screen of a user computing device.

25 Claims, 4 Drawing Sheets

(51) Int. Cl.
*G16H 50/20* (2018.01)
*G06T 7/00* (2017.01)
*A61Q 19/00* (2006.01)

(52) U.S. Cl.
CPC .. *A61Q 19/002* (2013.01); *G06T 2207/20081* (2013.01); *G06T 2207/20084* (2013.01); *G06T 2207/30088* (2013.01)

(56) References Cited

U.S. PATENT DOCUMENTS

| | | | |
|---|---|---|---|
| 2008/0091187 A1* | 4/2008 | Ferren | A61B 18/203 606/41 |
| 2009/0024023 A1 | 1/2009 | Welches et al. | |
| 2011/0016001 A1 | 1/2011 | Schieffelin | |
| 2017/0330264 A1 | 11/2017 | Youssef et al. | |
| 2018/0040053 A1 | 2/2018 | Robinson et al. | |
| 2018/0247365 A1 | 8/2018 | Cook et al. | |
| 2019/0166980 A1 | 6/2019 | Huang et al. | |
| 2019/0239752 A1* | 8/2019 | Dumitrescu | A61B 5/7264 |
| 2019/0355115 A1 | 11/2019 | Niebauer et al. | |
| 2020/0294234 A1 | 9/2020 | Rance et al. | |

* cited by examiner

DIGITAL IMAGING SYSTEMS AND METHODS OF ANALYZING PIXEL DATA OF AN IMAGE OF A USER'S BODY FOR DETERMINING A USER-SPECIFIC SKIN REDNESS VALUE OF THE USER'S SKIN AFTER REMOVING HAIR

FIELD

The present disclosure generally relates to digital imaging systems and methods, and more particularly to, digital imaging systems and methods for analyzing pixel data of an image of a user's body for determining a user-specific skin redness value of the user's skin after removing hair.

BACKGROUND

For many individuals, hair removal methods cause the skin to become red. An individual's reaction to a particular hair removal product or method may be a reaction to a product or to the way in which the individual applies or uses the product. For example, an individual's skin may become red after using a hair removal cream due to the individual's reaction to an ingredient in the cream or how long the individual has left the cream on their skin. As another example, an individual's skin may become red after or during shaving due to the individual's shaving technique (e.g., the individual may apply too much pressure for their skin or shave against the grain of the hair).

However, individuals generally are not aware of why skin redness occurs for their skin, and thus are not aware of how to decrease their skin redness while still effectively removing hair. Individuals also may not be aware of whether their reaction to a hair removal method or product is more severe than average, or whether their skin redness could be improved. While an individual may attempt to determine an effective combination of hair removal product(s) and/or method(s) based on generalized recommendations, the individual does not have feedback suited for or personalized for the individual based on the individual's skin redness after hair removal.

For the foregoing reasons, there is a need for digital imaging systems and methods for analyzing pixel data of an image of a user's body for determining a user-specific skin redness value of the user's skin after removing hair.

SUMMARY

Generally, as described herein, the digital systems and methods for analyzing pixel data of an image of a user's body for determining a user-specific skin redness value of the user's skin after removing hair provide a digital imaging and artificial intelligence (AI) based solution for overcoming problems that arise from incorrect use of different hair removal products and/or methods. The digital systems and methods allow a user to submit a specific user image to imaging server(s) (e.g., including its one or more processors), or otherwise a computing device (e.g., such as locally on the user's mobile device), where the imaging server(s) or user computing device implements or executes a skin redness model trained with pixel data of potentially 10,000 s (or more) images of individuals' skin after removing hair. The skin redness model may generate, based on a determined user-specific skin redness value, a user-specific electronic recommendation designed to address at least one feature identifiable within the pixel data comprising at least a portion of the user's skin after hair is removed from the skin.

For example, the at least one feature can comprise pixels or pixel data indicative of a degree of redness of the user's skin. In some embodiments, the user-specific recommendation (and/or product specific recommendation) may be rendered on a display screen of a user computing device of the user. In other embodiments, no transmission to the imaging server of the user's specific image occurs, where the user-specific recommendation (and/or product recommendation) may instead by generated by the skin redness model, executing and/or implemented locally on the user's mobile device and rendered, by a processor of the mobile device, on a display screen of the mobile device. In various embodiments, such rendering may include graphical representations, overlays, annotations, and the like for addressing the feature in the pixel data.

More specifically, as describe herein, a digital imaging method of analyzing pixel data of an image of a user's body for determining a user-specific skin redness value of the user's skin after removing hair is disclosed. The digital imaging method comprises aggregating, at one or more processors communicatively coupled to one or more memories, a plurality of training images of a plurality of individuals, each of the training images comprising pixel data of skin of a respective individual after removing hair. The method may also include training, by the one or more processors with the pixel data of the plurality of training images, a skin redness model comprising a skin redness scale and operable to output, across a range of the skin redness scale, skin redness values associated with a degree of skin redness ranging from least red to most red. The method may further include receiving, at the one or more processors, at least one image of a user, the at least one image captured by a digital camera, and the at least one image comprising pixel data of at least a portion of the user's skin after hair is removed from the at least a portion of the user's skin. Still further, the method may include analyzing, by the skin redness model executing on the one or more processors, the at least one image captured by the digital camera to determine a user-specific skin redness value of the user's skin. The method may also include generating, by the one or more processors based on the user-specific skin redness value, at least one user-specific electronic recommendation designed to address at least one feature identifiable within the pixel data of the at least a portion of the user's skin. The method may further include rendering, on a display screen of a user computing device, the at least one user-specific electronic recommendation.

In addition, as described herein, a digital imaging system is disclosed that is configured to analyze pixel data of an image of a user's body for determining a skin redness value of the user's skin after removing hair. The digital imaging system may comprise: an imaging server comprising a server processor and a server memory, an imaging application (app) configured to execute on a user computing device comprising a device processor and a device memory, and a skin redness model. The imaging app may be communicatively coupled to the imaging server. The skin redness model may comprise a skin redness scale and may be trained with pixel data of a plurality of training images of individuals. Further, the skin redness model may be operable to determine, across a range of the skin redness scale, skin redness values associated with a degree of skin redness ranging from least red to most red. The skin redness model may be configured to execute on the server processor or the device processor to cause the server processor or the device processor to receive at least one image of a user, the at least one image captured by a digital camera, and the at least one image comprising pixel data of at least a portion of the user's skin after hair is removed from the at least a portion of the user's skin. In addition, the skin redness model may cause the server processor or the device processor to analyze, by the skin redness model, the at least one image captured by the digital camera to determine a user-specific skin redness value of the user's skin. Further, the skin redness model may cause the server processor the device processor to generate, based on the user-specific skin redness value, at least one user-specific electronic recommendation designed to address at least one feature identifiable within the pixel data comprising the at least a portion of the user's skin. Still further, the skin redness model may cause the server processor or the device processor to render, on a display screen of the user computing device of the user, the at least one user-specific electronic recommendation.

Further, as described herein, a tangible, non-transitory computer-readable medium storing instructions for analyzing pixel data of an image of a user's body for determining a skin redness value of the user's skin after removing hair is disclosed. The instructions, when executed by one or more processors, cause the one or more processors to aggregate, at the one or more processers communicatively coupled to one or more memories, a plurality of training images of a plurality of individuals, each of the training images comprising pixel data of skin of a respective individual after removing hair. The instructions, when executed by the one or more processors, may further cause the one or more processors to train, with the pixel data of the plurality of training images, a skin redness model comprising a skin redness scale and operable to output, across a range of the skin redness scale, skin redness values associated with a degree of skin redness ranging from least red to most red. The instructions, when executed by the one or more processors, may further cause the one or more processors to receive at least one image of a user, the at least one image captured by a digital camera, and the at least one image comprising pixel data of at least a portion of the user's skin after hair is removed from the at least a portion of the user's skin. Still further, the instructions, when executed by the one or more processors, may cause the one or more processors to analyze, by the skin redness model executing on the one or more processors, the at least one image captured by the digital camera to determine a user-specific skin redness value of the user's skin. The instructions, when executed by the one or more processors, may also cause the one or more processors to generate, based on the user-specific skin redness value, at least one user-specific electronic recommendation designed to address at least one feature identifiable within the pixel data of the at least a portion of the user's skin. The instructions, when executed by the one or more processors, may further cause the one or more processors to render, on a display screen of a user computing device, the at least one user-specific electronic recommendation.

In accordance with the above, and with the disclosure herein, the present disclosure includes improvements in computer functionality or in improvements to other technologies at least because the disclosure describes that, e.g., an imaging server, or otherwise computing device (e.g., a user computing device), is improved where the intelligence or predictive ability of the imaging server or computing device is enhanced by a trained (e.g., machine learning trained) skin redness model. The skin redness model, executing on the imaging server or computing device, is able to accurately identify, based on pixel data of other individuals, a user-specific skin redness value and a user-specific electronic recommendation designed to address at least one feature identifiable within the pixel data of a specific user comprising the at least the portion of the user's skin after hair is removed from the at least a portion of the user's skin. That is, the present disclosure describes improvements in the functioning of the computer itself or "any other technology or technical field" because an imaging server or user computing device is enhanced with a plurality of training images (e.g., 10,000 s of training images and related pixel data as feature data) to accurately predict, detect, or determine pixel data of a user-specific images, such as newly provided customer images. This improves over the prior art at least because existing systems lack such predictive or classification functionality and are simply not capable of accurately analyzing user-specific images to output a predictive result to address at least one feature identifiable within the pixel data comprising the at least the portion of the user's skin.

For similar reasons, the present disclosure relates to improvements to other technologies or technical fields at least because the present disclosure describes or introduces improvements to computing devices in the field of hair removal or hair removal devices (e.g., shaving razors, light based hair removal devices, epilators, etc.), whereby the trained skin redness model executing on the imaging server or user computing device improves the field of hair removal and/or hair removal devices with digital and/or artificial intelligence based analysis of user or individual images to output a predictive result to address at least one feature identifiable within the user-specific pixel data comprising the at least the portion of the user's skin after hair is removed.

In addition, the present disclosure includes applying certain of the claim elements with, or by use of, a particular machine, e.g., in embodiments involving a razor or other hair removal device (e.g., an epilator or a light based hair removal device) that removes hair, where skin from which hair is removed appears in training images used to train the skin redness model and further appears in the images submitted by a user to determine a user-specific redness value of the user's skin after hair is removed from the user's skin.

In addition, the present disclosure includes specific features other than what is well-understood, routine, conventional activity in the field, or adding unconventional steps that confine the claim to a particular useful application, e.g., analyzing pixel data of an image of a user's body for determining a skin redness value of the user's skin after removing hair, as described herein.

Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the system and methods disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein.

The Figures depict preferred embodiments for purposes of illustration only. Alternative embodiments of the systems and methods illustrated herein may be employed without departing from the principles of the invention described herein.

DETAILED DESCRIPTION OF THE INVENTION

Figure 1:
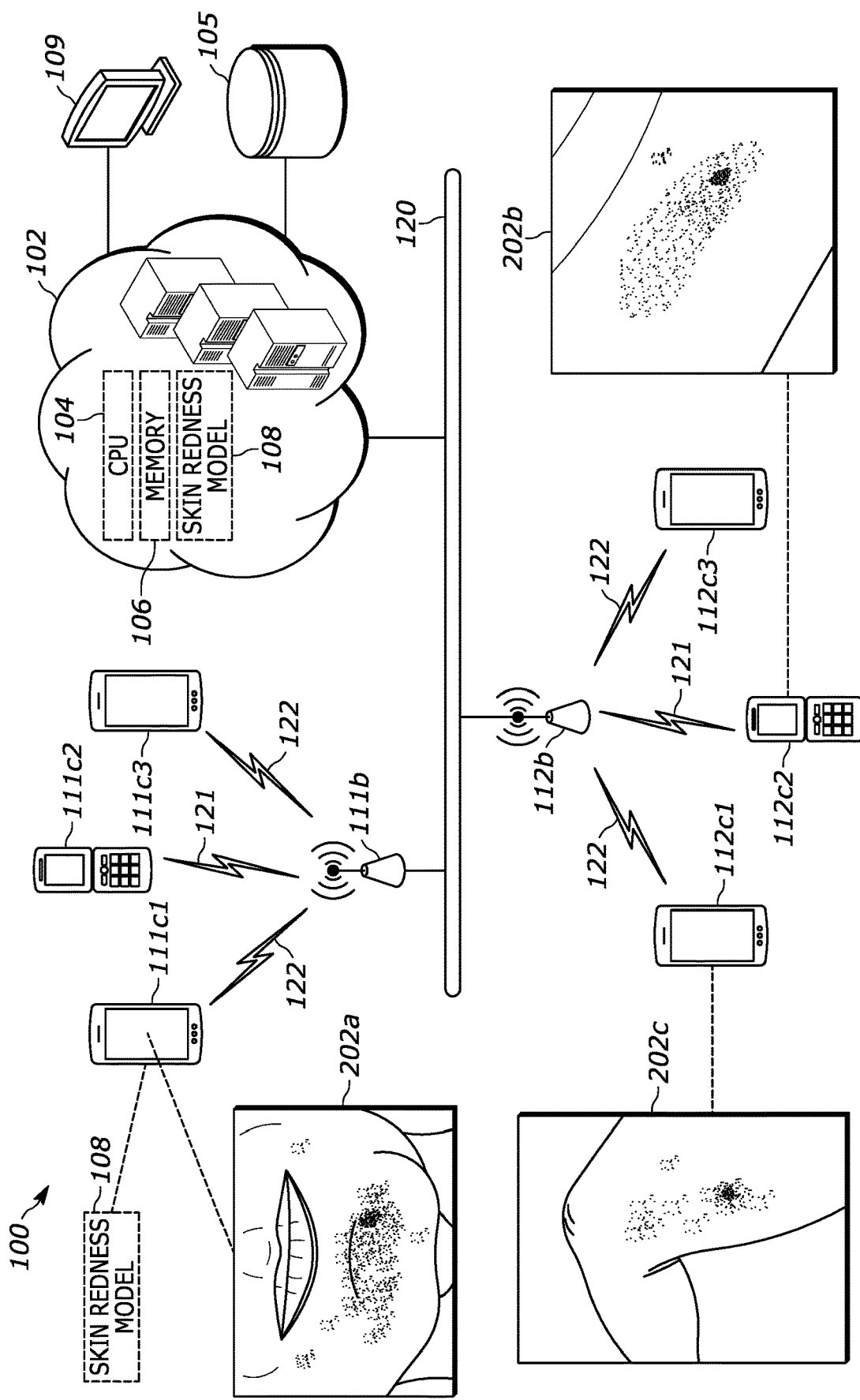
FIG. 1 illustrates an example digital imaging system configured to analyze pixel data of an image of a user's body for determining a skin redness value of the user's skin after removing hair, in accordance with various embodiments disclosed herein.

FIG. 1 illustrates an example digital imaging system 100 configured to analyze pixel data of an image (e.g., any one or more of images 202a, 202b, and/or 202c) of a user's body for determining a skin redness value of the user's skin after removing hair, in accordance with various embodiments disclosed herein. As referred to herein, a "body" may refer to any portion of the human body including the torso, waist, face, head, arm, leg, or other appendage or portion or part of the body thereof. In the example embodiment of FIG. 1, digital imaging system 100 includes server(s) 102, which may comprise one or more computer servers. In various embodiments server(s) 102 comprise multiple servers, which may comprise a multiple, redundant, or replicated servers as part of a server farm. In still further embodiments, server(s) 102 may be implemented as cloud-based servers, such as a cloud-based computing platform. For example, server(s) 102 may be any one or more cloud-based platform(s) such as MICROSOFT AZURE, AMAZON AWS, or the like. Server(s) 102 may include one or more processor(s) 104 as well as one or more computer memories 106. Server(s) 102 may be referred to herein as "imaging server(s)."

The memories 106 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. The memorie(s) 106 may store an operating system (OS) (e.g., Microsoft Windows, Linux, Unix, etc.) capable of facilitating the functionalities, apps, methods, or other software as discussed herein. The memorie(s) 106 may also store a skin redness model 108, which may be an artificial intelligence based model, such as a machine learning model trained on various images (e.g., images 202a, 202b, and/or 202c), as described herein. Additionally, or alternatively, the skin redness model 108 may also be stored in database 105, which is accessible or otherwise communicatively coupled to imaging server(s) 102. The memories 106 may also store machine readable instructions, including any of one or more application(s), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. For example, at least some of the applications, software components, or APIs may be, include, otherwise be part of, an imaging based machine learning model or component, such as the skin redness model 108, where each may be configured to facilitate their various functionalities discussed herein. It should be appreciated that one or more other applications may be envisioned and that are executed by the processor(s) 104.

The processor(s) 104 may be connected to the memories 106 via a computer bus responsible for transmitting electronic data, data packets, or otherwise electronic signals to and from the processor(s) 104 and memories 106 in order to implement or perform the machine readable instructions, methods, processes, elements or limitations, as illustrated, depicted, or described for the various flowcharts, illustrations, diagrams, figures, and/or other disclosure herein.

The processor(s) 104 may interface with the memory 106 via the computer bus to execute the operating system (OS). The processor(s) 104 may also interface with the memory 106 via the computer bus to create, read, update, delete, or otherwise access or interact with the data stored in the memories 106 and/or the database 104 (e.g., a relational database, such as Oracle, DB2, MySQL, or a NoSQL based database, such as MongoDB). The data stored in the memories 106 and/or the database 105 may include all or part of any of the data or information described herein, including, for example, training images and/or user images (e.g., either of which including any one or more of images 202a, 202b, and/or 202c) or other information of the user, including demographic, age, race, skin type, or the like.

The imaging server(s) 102 may further include a communication component configured to communicate (e.g., send and receive) data via one or more external/network port(s) to one or more networks or local terminals, such as computer network 120 and/or terminal 109 (for rendering or visualizing) described herein. In some embodiments, imaging server(s) 102 may include a client-server platform technology such as ASP.NET, Java J2EE, Ruby on Rails, Node.js, a web service or online API, responsive for receiving and responding to electronic requests. The imaging server(s) 102 may implement the client-server platform technology that may interact, via the computer bus, with the memories(s) 106 (including the applications(s), component(s), API(s), data, etc. stored therein) and/or database 105 to implement or perform the machine readable instructions, methods, processes, elements or limitations, as illustrated, depicted, or described for the various flowcharts, illustrations, diagrams, figures, and/or other disclosure herein. According to some embodiments, the imaging server(s) 102 may include, or interact with, one or more transceivers (e.g., WWAN, WLAN, and/or WPAN transceivers) functioning in accordance with IEEE standards, 3GPP standards, or other standards, and that may be used in receipt and transmission of data via external/network ports connected to computer network 120. In some embodiments, computer network 120 may comprise a private network or local area network (LAN). Additionally, or alternatively, computer network 120 may comprise a public network such as the Internet.

Imaging server(s) 102 may further include or implement an operator interface configured to present information to an administrator or operator and/or receive inputs from the administrator or operator. As shown in FIG. 1, an operator interface may provide a display screen (e.g., via terminal 109). Imaging server(s) 102 may also provide I/O components (e.g., ports, capacitive or resistive touch sensitive input panels, keys, buttons, lights, LEDs), which may be directly accessible via or attached to imaging server(s) 102 or may be indirectly accessible via or attached to terminal 109. According to some embodiments, an administrator or operator may access the imaging server 102 via terminal 109 to review information, make changes, input training data or images, and/or perform other functions.

As described above herein, in some embodiments, imaging server(s) 102 may perform the functionalities as discussed herein as part of a "cloud" network or may otherwise communicate with other hardware or software components within the cloud to send, retrieve, or otherwise analyze data or information described herein.

In general, a computer program or computer based product, application, or code (e.g., the model(s), such as AI models, or other computing instructions described herein) may be stored on a computer usable storage medium, or tangible, non-transitory computer-readable medium (e.g., standard random access memory (RAM), an optical disc, a universal serial bus (USB) drive, or the like) having such computer-readable program code or computer instructions embodied therein, wherein the computer-readable program code or computer instructions may be installed on or otherwise adapted to be executed by the processor(s) 104 (e.g., working in connection with the respective operating system in memories 106) to facilitate, implement, or perform the machine readable instructions, methods, processes, elements or limitations, as illustrated, depicted, or described for the various flowcharts, illustrations, diagrams, figures, and/or other disclosure herein. In this regard, the program code may be implemented in any desired program language, and may be implemented as machine code, assembly code, byte code, interpretable source code or the like (e.g., via Golang, Python, C, C++, C#, Objective-C, Java, Scala, ActionScript, JavaScript, HTML, CSS, XML, etc.).

As shown in FIG. 1, imaging server(s) 102 are communicatively connected, via computer network 120 to the one or more user computing devices 111c1-111c3 and/or 112c1-112c3 via base stations 111b and 112b. In some embodiments, base stations 111b and 112b may comprise cellular base stations, such as cell towers, communicating to the one or more user computing devices 111c1-111c3 and 112c1-112c3 via wireless communications 121 based on any one or more of various mobile phone standards, including NMT, GSM, CDMA, UMMTS, LTE, 5G, or the like. Additionally or alternatively, base stations 111b and 112b may comprise routers, wireless switches, or other such wireless connection points communicating to the one or more user computing devices 111c1-111c3 and 112c1-112c3 via wireless communications 122 based on any one or more of various wireless standards, including by non-limiting example, IEEE 802.11a/b/c/g (WIFI), the BLUETOOTH standard, or the like.

Any of the one or more user computing devices 111c1-111c3 and/or 112c1-112c3 may comprise mobile devices and/or client devices for accessing and/or communications with imaging server(s) 102. In various embodiments, user computing devices 111c1-111c3 and/or 112c1-112c3 may comprise a cellular phone, a mobile phone, a tablet device, a personal data assistance (PDA), a handheld device, a desktop device, or the like, including, by non-limiting example, an APPLE iPhone or iPad device or a GOOGLE ANDROID based mobile phone or tablet. Moreover, in various embodiments, user computing devices 111ca-111c3 and/or 112c1-112c3 may comprise a home or personal assistant, including, for example, GOOGLE HOME, AMAZON ALEXA, an ECHO SHOW device, or the like. In additional embodiments, user computing devices 111c1-111c3 and/or 112c1-112c3 may comprise a retail computing device. A retail computing device would be configured in the same or similar manner, e.g., as described herein for user computing devices 111c1-111c3, including having a processor and memory, for implementing, or communicating with (e.g., via server(s) 102), a pressure model 108 as described herein. However, a retail computing device may be located, installed, or otherwise positioned within a retail environment to allow users and/or customers of the retail environment to utilize the digital imaging systems and methods on site within the retail environment. For example, the retail computing device may be installed within a kiosk for access by a user. The user may then upload or transfer images (e.g., from a user mobile device) to the kiosk to implement the digital imaging systems and methods described herein. Additionally, or alternatively, the kiosk may be configured with a camera to allow the user to take new images (e.g., in a private manner where warranted) of himself or herself for upload and transfer. In such embodiments, the user or consumer himself or herself would be able to use the retail computing device to receive and/or have rendered a user-specific electronic recommendation, as described herein, on a display screen of the retail computing device. Additionally, or alternatively, the retail computing device may be a mobile device (as described herein) as carried by an employee or other personnel of the retail environment for interacting with users or consumers on site. In such embodiments, a user or consumer may be able to interact with an employee or otherwise personnel of the retail environment, via the retail computing device (e.g., by transferring images from a mobile device of the user to the retail computing device or by capturing new images by a camera of the retail computing device), to receive and/or have rendered a user-specific electronic recommendation, as described herein, on a display screen of the retail computing device. In addition, the one or more user computing devices 111c1-111c3 and/or 112c1-112c3 may implement or execute an operating system (OS) or mobile platform such as Apple's iOS and/or Google's Android operation system. Any of the one or more user computing devices 111c1-111c3 and/or 112c1-112c3 may comprise one or more processors and/or one or more memories for storing, implementing, or executing computing instructions or code, e.g., a mobile application, as described in various embodiments herein. As shown in FIG. 1, skin redness model 108 may also be stored locally on a memory of a user computing device (e.g., user computing device 111c1).

User computing devices 111c1-111c3 and/or 112c1-112c3 may comprise a wireless transceiver to receive and transmit wireless communications 121 and/or 122 to and from base stations 111b and/or 112b. Pixel based images 202a, 202b, and/or 202c may be transmitted via computer network 120 to imaging server(s) 102 for training of model(s) and/or imaging analysis as describe herein.

In addition, the one or more user computing devices 111c1-111c3 and/or 112c1-112c3 may include a digital camera and/or digital video camera for capturing or taking digital images and/or frames (e.g., which can be any one or more of images 202a, 202b, and/or 202c). Each digital image may comprise pixel data for training or implementing model(s), such as AI or machine learning models, as described herein. For example, a digital camera and/or digital video camera, e.g., of any of user computing devices 111c1-111c3 and/or 112c1-112c3, may be configured to take, capture, or otherwise generate digital images (e.g., pixel based images 202a, 202b, and/or 202c) and, at least in some embodiments, may store such images in a memory of a respective user computing devices.

Still further, each of the one or more user computer devices 111c1-111c3 and/or 112c1-112c3 may include a display screen for displaying graphics, images, text, product recommendations, data, pixels, features, and/or other such visualizations or information as described herein. In various embodiments, graphics, images, text, product recommendations, data, pixels, features, and/or other such visualizations or information may be received by server(s) 102 for display on the display screen of any one or more of user computer devices 111c1-111c3 and/or 112c1-112c3. Additionally, or alternatively, a user computer device may comprise, implement, have access to, render, or otherwise expose, at least in part, an interface or a guided user interface (GUI) for displaying text and/or images on its display screen.

Figure 2A:
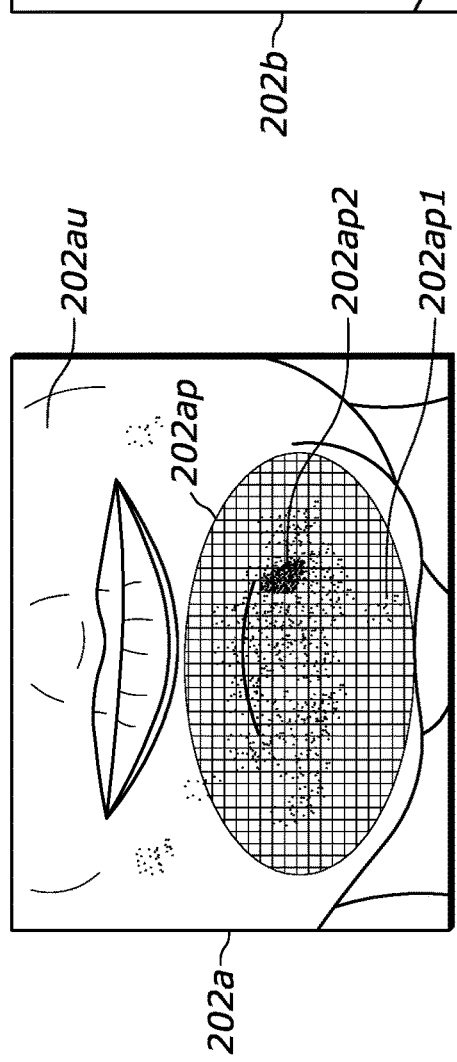
FIG. 2A illustrates an example image and its related pixel data that may be used for training and/or implementing a skin redness model, in accordance with various embodiments disclosed herein.
Figure 2B:
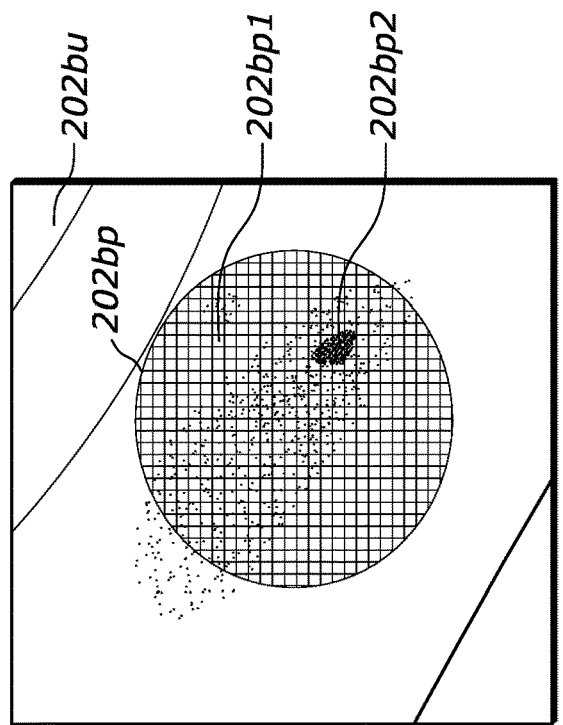
FIG. 2B illustrates a further example image and its related pixel data that may be used for training and/or implementing a skin redness model, in accordance with various embodiments disclosed herein.
Figure 2C:
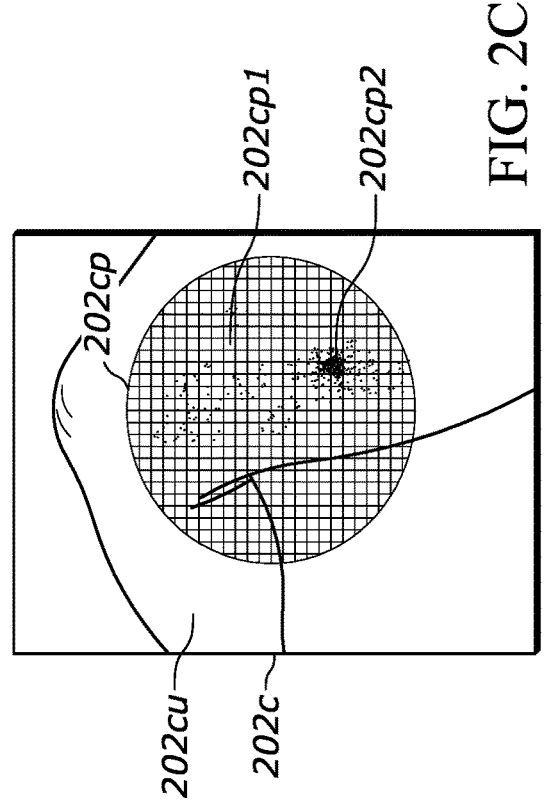
FIG. 2C illustrates a further example image and its related pixel data that may be used for training and/or implementing a skin redness model, in accordance with various embodiments disclosed herein.

FIGS. 2A-2C illustrate example images 202a, 202b, and 202c that may be collected or aggregated at imaging server(s) 102 and may be analyzed by, and/or used to train, a skin redness model (e.g., an AI model such as a machine learning imaging model as describe herein). Each of these images may comprise pixel data (e.g., RGB data) corresponding representing feature data and corresponding to each of the personal attributes of the respective users 202au, 202bu, and 202cu, within the respective image. The pixel data may be captured by a digital camera of one of the user computing devices (e.g., one or more user computer devices 111c1-111c3 and/or 112c1-112c3).

Generally, as described herein, pixel data (e.g., pixel data 202ap, 202bp, and/or 202cp) comprises individual points or squares of data within an image, where each point or square represents a single pixel (e.g., pixel 202ap1 and pixel 202ap2) within an image. Each pixel may be a specific location within an image. In addition, each pixel may have a specific color (or lack thereof). Pixel color may be determined by a color format and related channel data associated with a given pixel. For example, a popular color format includes the red-green-blue (RGB) format having red, green, and blue channels. That is, in the RGB format, data of a pixel is represented by three numerical RGB components (Red, Green, Blue), that may be referred to as referred to as a channel data, to manipulate the color of pixel's area within the image. In some implementations, the three RGB components may be represented as three 8-bit numbers for each pixel. Three 8-bit bytes (one byte for each of RGB) is used to generate 24 bit color. Each 8-bit RGB component can have 256 possible values, ranging from 0 to 255 (i.e., in the base 2 binary system, an 8 bit byte can contain one of 256 numeric values ranging from 0 to 255). This channel data (R, G, and B) can be assigned a value from 0 to 255 and be used to set the pixel's color. For example, three values like (250, 165, 0), meaning (Red=250, Green=165, Blue=0), can denote one Orange pixel. As a further example, (Red=255, Green=255, Blue=0) means Red and Green, each fully saturated (255 is as bright as 8 bits can be), with no Blue (zero), with the resulting color being Yellow. As a still further example, the color black has an RGB value of (Red=0, Green=0, Blue=0) and white has an RGB value of (Red=255, Green=255, Blue=255). Gray has the property of having equal or similar RGB values. So (Red=220, Green=220, Blue=220) is a light gray (near white), and (Red=40, Green=40, Blue=40) is a dark gray (near black).

In this way, the composite of three RGB values creates the final color for a given pixel. With a 24-bit RGB color image using 3 bytes there can be 256 shades of red, and 256 shades of green, and 256 shades of blue. This provides 256×256×256, i.e., 16.7 million possible combinations or colors for 24 bit RGB color images. In this way, the pixel's RGB data value shows how much" of each of Red, and Green, and Blue the pixel is comprised of. The three colors and intensity levels are combined at that image pixel, i.e., at that pixel location on a display screen, to illuminate a display screen at that location with that color. It is to be understood, however, that other bit sizes, having fewer or more bits, e.g., 10-bits, may be used to result in fewer or more overall colors and ranges. Further, it is to be understood that the pixel data may contain additional or alternative color format and channel data. For example, the pixel data may include color data expressed in a hue saturation value (HSV) format or hue saturation lightness (HSL) format.

As a whole, the various pixels, positioned together in a grid pattern, form a digital image (e.g., pixel data 202ap, 202bp, and/or 202cp). A single digital image can comprise thousands or millions of pixels. Images can be captured, generated, stored, and/or transmitted in a number of formats, such as JPEG, TIFF, PNG and GIF. These formats use pixels to store represent the image.

FIG. 2A illustrates an example image 202a and its related pixel data (e.g., pixel data 202ap) that may be used for training and/or implementing a skin redness model (e.g., skin redness model 108), in accordance with various embodiments disclosed herein. Example image 202a illustrates a user 202au or individual after removing hair, at a body area location comprising the user's chin. Image 202a is comprised of pixel data, including pixel data 202ap. Pixel data 202ap includes a plurality of pixels including pixel 202ap1 and pixel 202ap2. Pixel 202ap1 is a pixel positioned in image 202a where user 202au has little or no redness on the user's skin (i.e., the pixel 202ap1 includes the user's baseline skin color for the user's body or for the user's chin). Pixel 202ap2 is a pixel positioned in image 202a comprising a portion of the user's skin that has a higher degree of redness than the skin depicted by pixel 202ap1 (e.g., pixel 202ap2 is a pixel with a high R value). Pixel data 202ap includes various remaining pixels including remaining portions of the user's chin and face, including portions that indicate various degrees of redness.

FIG. 2B illustrates a further example image 202b and its related pixel data (e.g., pixel data 202bp) that may be used for training and/or implementing a skin redness model (e.g., skin redness model 108), in accordance with various embodiments disclosed herein. Example image 202b illustrates a user 202bu or individual after removing hair, at a body location comprising the user's neck. Image 202b is comprised of pixel data, including pixel data 202bp. Pixel data 202*bp* includes a plurality of pixels including pixel 202*bp*1 and pixel 202*bp*2. Pixel 202*bp*1 is a pixel positioned in image 202*b* where user 202*bu* has little or no redness on the user's skin (i.e., the pixel 202*bp*1 includes the user's baseline skin color for the user's body or for the user's neck). Pixel 202*bp*2 is a pixel positioned in image 202*b* comprising a portion of the user's skin that has a higher degree of redness than the skin depicted by pixel 202*bp*1 (e.g., pixel 202*b*2 is a pixel with a high R value). Pixel data 202*bp* includes various remaining pixels including remaining portions of the user's neck, including portions that indicate various degrees of redness.

FIG. 2C illustrates a further example image 202*cu* and its related pixel data (e.g., 202*cp*) that may be used for training and/or implementing a skin redness model (e.g., skin redness model 108), in accordance with various embodiments disclosed herein. Example image 202*c* illustrates a user 202*cu* or individual after removing hair, at a body area location comprising the user's leg. Image 202*c* is comprised of pixel data, including pixel data 202*cp*. Pixel data 202*cp* includes a plurality of pixels including pixel 202*cp*1 and pixel 202*cp*2. Pixel 202*cp*1 is a pixel positioned in image 202*c* where user 202*cu* has little or no redness on the user's skin (i.e., the pixel 202*cp*1 includes the user's baseline skin color for the user's body or for the user's leg). Pixel 202*cp*2 is a pixel positioned in image 202*c* comprising a portion of the user's skin that has a higher degree of redness than the skin depicted by pixel 202*cp*1 (e.g., pixel 202*cp*2 is a pixel with a high R value). Pixel data 202*cp* includes various remaining pixels including remaining portions of the user's leg, including portions that indicate various degrees of redness.

Figure 3:
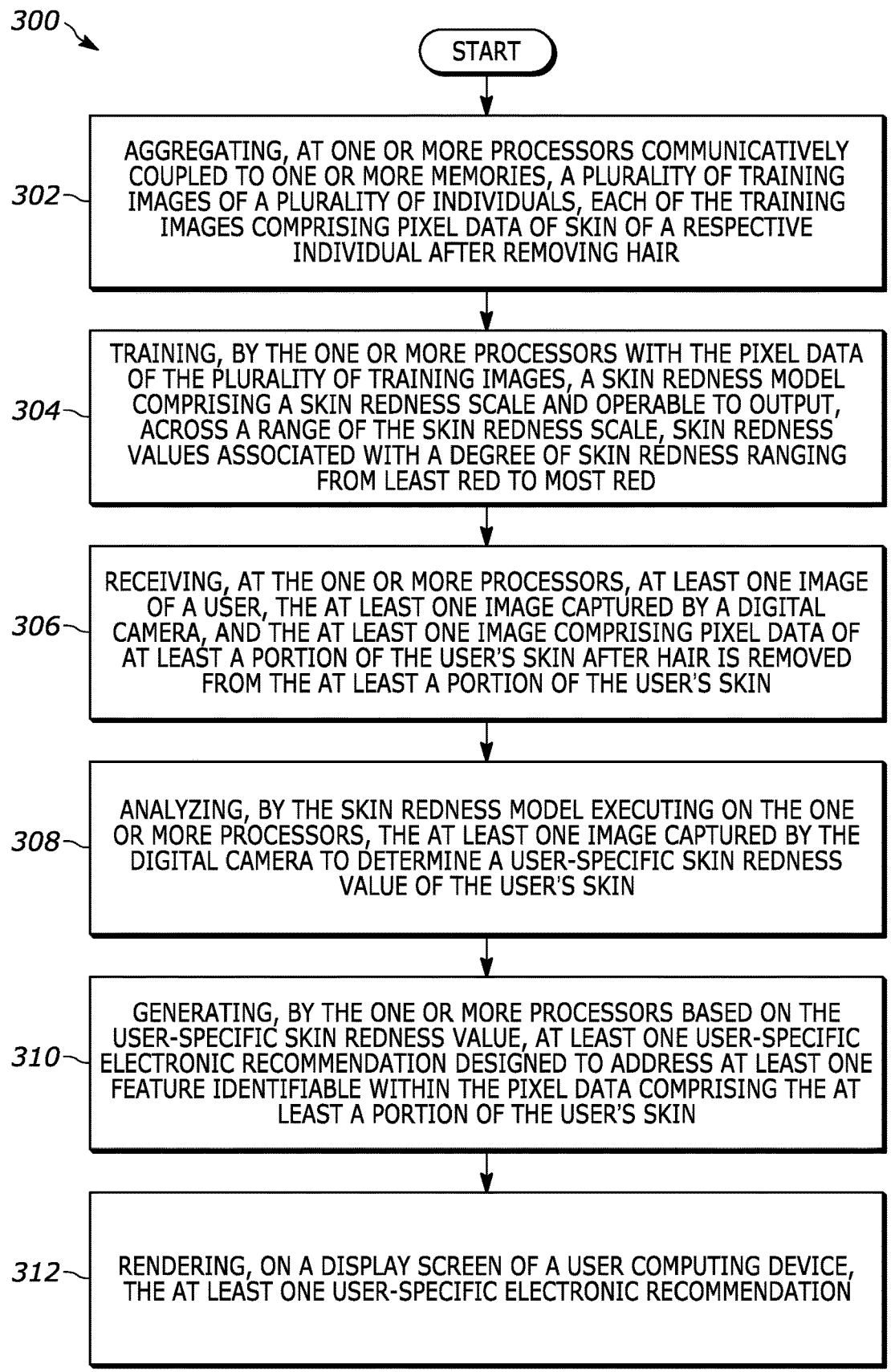
FIG. 3 illustrates a diagram of a digital imaging method of analyzing pixel data of an image of a user's body for determining a skin redness value of the user's skin after removing hair, in accordance with various embodiments disclosed herein.

FIG. 3 illustrates a diagram of a digital imaging method 300 of analyzing pixel data of an image (e.g., any of images 202*a*, 202*b*, and/or 202*c*) of a user's body for determining a user-specific skin redness value of the user's skin after removing hair, in accordance with various embodiments disclosed herein. Images, as described herein, are generally pixel images as captured by a digital camera (e.g., a digital camera of user computing device 111*c*1). In some embodiments, an image may comprise or refer to a plurality of images such as a plurality of images (e.g., frames) as collected using a digital video camera. Frames comprise consecutive images defining motion, and can comprise a movie, a video, or the like.

At block 302, method 300 comprises aggregating, at one or more processors communicatively coupled to one or more memories, a plurality of training images of a plurality of individuals, each of the training images comprising pixel data of skin of a respective individual after removing hair.

In some embodiments, the one or more processors may be included in server 102 (e.g., the one or more processors may be the one or more processors 104 of the server 102), and may receive the plurality of training images via a computer network, such as computer network 120. In such embodiments, additional steps of method 300 (such as one or more of blocks 304-312) may be performed by the server 102. In other embodiments, the one or more processors may be included in a user computing device, such as one of user computer devices 111*c*1-111*c*3 or 112*c*1-112*c*3. In such embodiments, additional steps of method 300 (such as one or more of blocks 304-312) may be performed by the user computing device.

In further embodiments, different steps of method 300 may be performed by different computing devices. For example, the server 102 may aggregate the plurality of training images and train skin redness model 108. A user computing device (such as user computing device 111*c*1) may receive the skin redness model 108 from the server 102 and store the skin redness model 108. The user computing device then may receive an image from a user and analyze the image using the stored skin redness model 108. In some implementations, the user computing device 108 may not store the skin redness model 108, but may access the skin redness model 108 stored at the server 102 to analyze any received images (e.g., by interacting with the skin redness model 108 via an API that exposes the skin redness model 108 to the user computing device).

As mentioned above, the training images include pixel data of individuals after hair is removed from the individuals. For example, a first training image may include an image of a first individual after hair is removed from the individual's leg. Similarly, a second training image may include an image of a second individual after hair is removed from the individual's underarm. The training images may depict, for each respective individual, the face (e.g., a view of the individual's face from the front or the side), cheek, neck, jaw, head, groin, underarm, chest, back, leg, arm, or bikini area, and may be zoomed in so as to show a portion of the individual's skin where hair has been removed. The hair may have been removed from each respective individual in a variety of ways (e.g., by a wet razor, a dry shaver, an epilator, a light based hair removal device, a depilatory cream, a wax, etc.). The training images may be captured in real-time (or near real-time) as the hair is removed, or after the hair is removed (e.g., within an hour after the hair is removed). Further, the plurality of training images may include thousands (e.g., 10,000*s*) of images.

At block 304 method 300 comprises training, by the one or more processors with the pixel data of the plurality of training images, a skin redness model, such as the skin redness model 108, comprising a skin redness scale and operable to output, across a range of the skin redness scale, skin redness values associated with a degree of skin redness ranging from least red to most red. In various embodiments, the skin redness model may be an artificial intelligence (AI) based model trained with at least one AI algorithm, as discussed in further detail below.

The skin redness scale can be an internalized scale or otherwise custom scale, unique to the skin redness model (e.g., skin redness model 108), where a least or small skin redness value may be determined from an image or set of images having skin areas with low skin redness values, i.e., images where the pixel data indicates that a skin area has low redness or is the same as or is similar to a user's baseline color, which may be images of skin before hair is removed. Similarly, a most or large redness value may be determined from an image or set of images having skin areas with high redness values, i.e., images where the pixel data indicates that a skin area is more red than the user's baseline skin color.

In some embodiments, the skin redness scale may be a percentage scale, e.g., outputting skin redness values from 0% to 100%, where 0% represents least red and 100% represents most red. Values can range across this scale, where a skin redness value of 67% represents one or more pixels of a skin area detected within an image that has a higher skin redness value than a skin redness value of 10% as detected for one or more pixels of a skin area within the same image or a different image (of the same or different user).

In some embodiments, the skin redness scale may be a numerical or decimal based scale, e.g., outputting skin redness values, e.g., from 0 to 10, where 0 represents least red and 10 represents most red. Values can range across this scale where a skin redness value of 7 represents one or more pixels of a skin area detected within an image that has a higher skin redness value than a skin redness value of 3 as detected for one or more pixels of a skin area within the same image or a different image (of the same or different user). In some embodiments, the skin redness scale may be a scale based on the RGB color format (e.g., an "R" or redness component ranging from 0 (least red) to 255 (most red)), on another suitable color format, such as the HSV model.

The skin redness scale may be adjusted or normalized based on a baseline skin color (i.e., a color of the skin before removing hair and/or a color of the skin after removing hair that does not have additional redness caused by removing hair). For example, skin redness model 108 may be trained to adjust the skin redness scale when applied to an image, such that if an individual depicted in the image has red tones or hues in their baseline skin color, this baseline skin color would still be classified as "least red." Training skin redness model 108 to determine skin redness values thus may include training skin redness model 108 to determine skin redness as defined as an excess of redness from an individual's baseline skin color.

Skin redness values may be determined at the pixel level or for a given skin area (e.g., one or more pixels) in an image. In some embodiments, a comprehensive skin redness value, which can be a user-specific skin redness value as described herein, may be determined by averaging (or otherwise statistically analyzing) skin redness values for one or more pixels of a given skin area.

Training of skin redness model 108 involves image analysis of the training images to configure weights of skin redness model 108, and its underlying algorithm (e.g., machine learning or artificial intelligence algorithm) used to predict and/or classify future images. For example, in various embodiments herein, generation of skin redness model 108 involves training skin redness model 108 with the plurality of training images of a plurality of individuals, where each of the training images comprise pixel data of a respective individual after the individual's hair is removed from the all or a portion of the skin depicted in the training image. In some embodiments, one or more processors of a server or a cloud-based computing platform (e.g., imaging server(s) 102) may receive the plurality of training images of the plurality of individuals via a computer network (e.g., computer network 120). In such embodiments, the server and/or the cloud-based platform may train the skin redness model with the pixel data of the plurality of training images.

In various embodiments, a machine learning imaging model, as described herein (e.g., skin redness model 108), may be trained using a supervised or unsupervised machine learning program or algorithm. The machine learning program or algorithm may employ a neural network, which may be a convolutional neural network, a deep learning neural network, or a combined learning module or program that learns in two or more features or feature datasets (e.g., pixel data) in a particular areas of interest. The machine learning programs or algorithms may also include natural language processing, semantic analysis, automatic reasoning, regression analysis, support vector machine (SVM) analysis, decision tree analysis, random forest analysis, K-Nearest neighbor analysis, naïve Bayes analysis, clustering, reinforcement learning, and/or other machine learning algorithms and/or techniques. In some embodiments, the artificial intelligence and/or machine learning based algorithms may be included as a library or package executed on imaging server(s) 102. For example, libraries may include the TENSORFLOW based library, the PYTORCH library, and/or the SCIKIT-LEARN Python library.

Machine learning may involve identifying and recognizing patterns in existing data (such as training a model based on pixel data within images having pixel data of a respective individual after removing hair) in order to facilitate making predictions or identification for subsequent data (such as using the model on new pixel data of a new individual in order to determine a user-specific skin redness value of the user's skin after hair is removed from the specific user's skin).

Machine learning model(s), such as the skin redness model described herein for some embodiments, may be created and trained based upon example data (e.g., "training data" and related pixel data) inputs or data (which may be termed "features" and "labels") in order to make valid and reliable predictions for new inputs, such as testing level or production level data or inputs. In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the server, computing device, or otherwise processor(s), to predict, based on the discovered rules, relationships, patterns, or model, an expected output.

In unsupervised machine learning, the server, computing device, or otherwise processor(s), may be required to find its own structure in unlabeled example inputs, where, for example multiple training iterations are executed by the server, computing device, or otherwise processor(s) to train multiple generations of models until a satisfactory model, e.g., a model that provides sufficient prediction accuracy when given test level or production level data or inputs, is generated. The disclosures herein may use one or both of such supervised or unsupervised machine learning techniques.

Image analysis may include training a machine learning based model (e.g., the skin redness model) on pixel data of images of one or more individuals after removing hair. Additionally, or alternatively, image analysis may include using a machine learning imaging model, as previously trained, to determine, based on the pixel data (e.g., including their RGB values) of the one or more images of the user, a user-specific redness value of the user's skin after hair is removed from the user's skin. The weights of the model may be trained via analysis of various RGB values of individual pixels of a given image. For example, dark or low RGB values (e.g., a pixel with values R=25, G=28, B=31) may indicate a pressed or loaded area of the user's skin. A red toned RGB value (e.g., a pixel with values R=215, G=90, B=85) may indicate irritated skin. A lighter RGB value (e.g., a pixel with R=229, G=194, and B=152) may indicate a lighter value, such as a baseline skin color of a particular individual. Together, when a pixel with a red toned RGB value is positioned within a given image, or is otherwise surrounded by a group or set of pixels having baseline-skin toned colors, then that may indicate an area on the skin where skin redness or irritation occurs, as identified within the given image. In this way, pixel data (e.g., detailing one or more features of an individual or the image, such as areas of redness on the user's skin, the user's baseline skin color, body area locations depicted in the images, surface area of skin depicted in the image, how hair was removed, how much time after removing hair the image was captured, etc.) of 10,000 s of training images may be used to train or use a machine learning imaging model to determine a user-specific redness value of the user's skin after hair is removed from the user's skin.

The training images may include features within the pixel data or may be accompanied by features describing the training images. For example, features within the pixel data may include areas of redness of the user's skin, areas of the user's baseline skin color, and body area locations of the images. Accompanying features that describe the training image that may be provided to skin redness model 108 during training, or may be within the pixel data and determined by skin redness model 108 during training, include how the hair was removed from the individual (e.g., by a wet razor, a dry shaver, an epilator, a light based hair removal device, a depilatory cream, a wax, etc., or, in the case of shaving, the type and/or direction of strokes that the individual made), whether the individual applied any pre-hair removal preparation products or post-hair removal remedial products, the body area location where the hair was removed from the skin, and how long after hair was removed the image was captured (e.g., during hair removal, a minute after hair removal, an hour after hair removal, etc.). In some implementations, training images may include images of the individuals before hair was removed, and the images may be labeled as such, such that skin redness model 108 can be trained to identify an individual's baseline skin color (i.e., the color of the individual's skin before removing hair and/or a color of the skin after removing hair that does not have additional redness caused by removing hair).

In some embodiments, training, by the one or more processors (e.g., of imaging server(s) 102 with the pixel data of the plurality of training images, the skin redness model (e.g., skin redness model 108) comprises training the skin redness model (e.g., skin redness model 108) to determine color values of pixels included in the pixel data of the at least a portion of the user's kin to determine the user-specific skin redness value. Said another way, training skin redness model 108 to determine skin redness values may include training, with the pixel data of the plurality of training images, skin redness model 108 to determine color values of pixels included in the pixel data of an image. In such embodiments, the skin redness model may be trained to recognize that pixels with given R values or combinations of RGB values indicate a redness area on the skin. For example, for image 202a, pixel 202ap1 is a baseline-skin color pixel positioned in image 202a. Pixel 202ap2 is a red toned color pixel positioned in image 202a. Pixel data 202ap includes various remaining pixels including remaining portions of the user's chin and face of varying degrees of redness. Skin redness model 108 may be trained to recognize (by assigning greater weights to redder pixels) that such redder pixels (redder when compared to the user's baseline skin color) indicate an area of skin redness after hair removal.

Similarly, skin redness model 108 may be trained to determine degrees of redness that depend on other factors in addition to the color values of the pixels. For example, skin redness model 108 may also be trained to determine skin redness values based on the surface area of red portions of the skin, or based on the presence of certain patterns or spacing of red areas that skin redness model 108 identifies.

As mentioned previously, skin redness values may be determined at the pixel level or for a given skin area (e.g., one or more pixels) in an image. In some embodiments, a comprehensive skin redness value, which can be a user-specific skin redness value as described herein, may be determined by averaging (or otherwise statistically analyzing) skin redness values for one or more pixels of a given skin area. For example, depending on the embodiment, the skin redness values may be an average or other numerical representation of the redness of the image as a whole, of a portion of the image determined to include skin, of a portion of the image determined to include skin with a redness above the skin's baseline color, or of a portion of the image determined to include skin where hair has been removed. In other embodiments, the skin redness values may be a highest redness of the pixel data included in the image.

In various embodiments, a skin redness model (e.g., skin redness model 108) may be further trained, by one or more processors (e.g., imaging server(s) 102), with the pixel data of the plurality of training images, to output one or more location identifiers indicating one or more corresponding body area locations of respective individuals. In such embodiments, the skin redness model (e.g., skin redness model 108), executing on the one or more processors (e.g., imaging server(s) 102) and analyzing the at least one image of the user, can determine a location identifier indicating a body area location of the user's body or body area. For example, body area locations may comprise a user's face, a user's cheek, a user's neck, a user's jaw, a user's chin, a user's head, a user's groin, a user's underarm, a user's chest, a user's back, a user's leg, a user's arm, or a user's bikini area. For example, each of images 202a, 202b, and 202c illustrate example body area locations including a user's chin or face, a user's neck, and a user's leg, respectively.

With reference to FIG. 3, at block 306 method 300 comprises receiving, at the one or more processors (e.g., imaging server(s) 102 and/or a user computing device, such as user computing device 111c1), at least one image of a user. The at least one image may be captured by a digital camera. In addition, the at least one image may comprise pixel data of at least a portion of the user's skin after hair is removed from the at least a portion of the user's skin.

The digital camera may be a digital camera of one of the user computing devices (e.g., one or more user computing devices 111c1-111c3 and/or 112c1-112c3). In some embodiments, the at least one image of at least a portion of the user's skin may include a plurality of images. In such embodiments, the plurality of images may be captured using a digital video camera of one of the user computing devices. The digital camera may capture the at least one image within one hour after the hair is removed. In some embodiments, the digital camera may capture the at least one image during hair removal (i.e., as the hair is being removed from the user's skin) and/or directly after hair removal. The hair may have been removed from the user's skin via any hair removal technique and/or device (e.g., by a wet razor, a dry shaver, an epilator, a light based hair removal device, a depilatory cream, and/or a wax). In addition to receiving the at least one image of the portion of the user's skin after removing hair, the one or more processors may receive additional information (e.g., from the user computing device or an application executing on the user computing device) regarding the at least one image, such as what hair removal technique or device was used to remove the hair, or how long after removing the hair the at least one image was captured. In some embodiments, the one or more processors may receive an additional image of the user's skin before removing hair, which the one or more processors may use to determine a baseline skin color of the user's skin.

At block 308 method 300 comprises analyzing, by the skin redness model executing on the one or more processors (e.g., imaging server(s) 102 and/or a user computing device, such as user computing device 111c1), the at least one image captured by the digital camera to determine a user-specific skin redness value of the user's skin. The user-specific redness value may be an average or other numerical representation of the redness of the at least one image as a whole, of a portion of the at least one image determined to include skin, of a portion of the image determined to include skin with a redness above the user's baseline skin color, or of a portion of the image determined to include skin where hair has been removed. In some embodiments, the user-specific redness value may be a skin redness value of the pixel corresponding to the highest redness value of the pixel data included in the image.

If skin redness model 108 has been trained to identify body area locations, analyzing the at least one image may also include determining a location identifier indicating a body area location of the user's body or body area (e.g., a body area location corresponding to a user's face, cheek, neck, jaw, chin, head, groin, underarm, chest, back, leg, arm, or bikini area).

At block 310 method 300 comprises generating, by the one or more processors (e.g., imaging server(s) 102 and/or a user computing device, such as user computing device 111c1) based on the user-specific skin redness value, at least one user-specific electronic recommendation designed to address at least one feature identifiable within the pixel data of the at least a portion of the user's skin. The at least one user-specific electronic recommendation may include, for example, a product recommendation for a manufactured product. For example, the product recommendation may be for a manufactured product (e.g., pre-hair removal gel or balm, shaving gel, shaving cream, after shave gel or balm, post-hair removal gel or balm, shaving razor, shaving blade (s), etc.) that will address a feature identifiable within the pixel data (e.g., that will reduce skin redness identified within the pixel data). The at least one user-specific recommendation may include instructions for treating, with the manufactured product, the at least one feature (e.g., apply the recommended product before or after shaving to reduce skin redness). In some embodiments, the one or more processors may generate a modified image based on the at least one image, where the modified image depicts how the user's skin is predicted to appear after treating the at least one feature with the manufactured product. Additionally or alternatively, in some embodiments, the one or more processors may generate a modified user-specific skin redness value that the user's skin is predicted to have after treating the at least one feature with the manufactured product.

As another example, the at least one user-specific electronic recommendation may include a recommended behavior that the user may practice to reduce their skin redness. The behavior may be recommended based on the user-specific skin redness value, and may, for example, be selected from two or more available behaviors based on the user-specific skin redness value. In some embodiments, the behavior may be a hair removal behavior. For instance, if the user indicates, or skin redness model 108 determines, that the hair was removed with a razor, the user-specific electronic recommendation may suggest a different shaving technique, such as shaving with the grain of the hair, to improve skin redness, or may suggest a different hair removal method to remove the hair. In various embodiments, the behavior may be a behavior that does not include hair removal, or may be a combination of one or more hair removal behaviors and one or more other types of behaviors. Example behaviors include skin treatments (e.g., how or when to apply a pre- or post-hair removal product or skin product), cosmetic treatments (e.g., applying a makeup product), personal hygiene behaviors, showering behaviors (e.g., take a shower prior to shaving), or the like.

At block 312 method 300 comprises rendering, on a display screen of a user computing device, the at least one user-specific electronic recommendation. Depending on the embodiment, method 300 may include rendering the at least one image and/or (if generated) a modified image depicting how the user's skin is predicted to appear after treating the at least one feature with the manufactured product (e.g., rendering the at least one image side-by-side with the modified image to allow a user to compare the images), and/or rendering (if generated) a modified user-specific skin irritation value that the user's skin is predicted to have after treating the at least one feature with the manufactured product. A user computing device may comprise at least one of a mobile device, a tablet, a handheld device, or a desktop device, for example, as described herein for FIG. 1. In some embodiments, the user computing device (e.g., user computing device 111c1) may receive the at least one image comprising the pixel data of the at least a portion of the user's skin. In such embodiments, the user computing device may execute the skin redness model (e.g., skin redness model 108) locally and generate, based on output of the skin redness model (e.g., skin redness model 108), the user-specific recommendation. The user computing device 111c1 may then render the user-specific recommendation on its display screen.

Additionally, or alternatively, in other embodiments, the imaging server(s) 102 may analyze the user image remote from the user computing device to determine the user-specific skin redness value and/or user-specific electronic recommendation designed to address at least one feature identifiable within the pixel data comprising the at least a portion of the user's skin after removing hair from the at least a portion of the user's skin. For example, in such embodiments, an imaging server or a cloud-based computing platform (e.g., imaging server(s) 102) receives, across computer network 120, the at least one image comprising the pixel data of the at least a portion of the user's skin. The server or a cloud-based computing platform may then execute skin redness model (e.g., skin redness model 108) and generate, based on output of the skin redness model (e.g., skin redness model 108), the user-specific recommendation. The server or a cloud-based computing platform may then transmit, via the computer network (e.g., computer network 120), the user-specific recommendation to the user-computing device for rendering on the display screen of the user computing device.

In some embodiments, the user may submit a new image to the skin redness model for analysis as described herein. In such embodiments, one or more processors (e.g., imaging server(s) 102 and/or a user computing device, such as user computing device 111c1) may receive a new image of the user. The new image may been captured by a digital camera of user computing device 111c1. The new image may comprise new pixel data of at least a portion of the user's skin after hair is removed from the at least a portion of the user's skin. The portion of skin depicted in the new image may be the same or a different portion of the skin as the skin depicted in the image received at block 306. For example, the new image may be captured at a later time (e.g., the initial image may be captured directly after removing hair and the new image may be captured an hour after removing hair) or after a second hair removal. The skin redness model (e.g., skin redness model 108) may then analyze, on the one or more processors (e.g., imaging server(s) 102 and/or a user computing device, such as user computing device 111c1), the new image captured by the digital camera to determine a new user-specific skin redness value. In some examples, the one or more processors may generate a delta skin redness value based on a comparison between the new user-specific skin redness value and the initial or previous user-specific skin redness value. A new user-specific electronic recommendation or comment may be generated, based on the new user-specific skin redness value and/or based on the delta skin redness value, regarding at least one feature identifiable within the pixel data of the new image. In some embodiments, the new user-specific electronic recommendation or comment may include a comparative comment based on a comparison between the new user-specific skin redness value and the initial or previous user-specific skin redness value. For example, the comparative comment may describe the changes or improvements in the skin redness of the user's skin. The new user-specific recommendation or comment (e.g., message) may then be rendered on a display screen of a user computing device of the user. For example, based on the new image, skin redness model 108 may determine a lower (or higher) user-specific skin redness value that the user-specific skin redness value determined at block 308, and may generate a new recommendation or comment reflecting the lower (or higher) user-specific skin redness value. The recommendation may recommend how the user may address their skin redness value via a product or change in behavior, and the one or more processors may initialize shipment of the product.

In some embodiments, a user-specific electronic recommendation may be displayed on the display screen of a user computing device (e.g., user computing device 111c1) with a graphical representation of the user's skin as annotated with one or more graphics or textual renderings corresponding to the user-specific skin redness value. For example, the user computing device may display the at least one image of at least a portion of the user's skin, or a portion of the at least one image (e.g., a portion of the at least one image indicating a high degree of skin redness or a higher degree of skin redness than other portions of the at least one image). In some examples, the user computing device may display the at least one image of at least a portion of the user's skin and a new image (discussed above) (or graphical representations thereof) and may display annotations regarding a comparison between the at least one image and the new image, such as the comparative comment discussed above. For example, the user computing device may display the at least one image and the new image side-by-side to facilitate comparison. The graphics and textual renderings that may be rendered in addition to the user-specific electronic recommendation are discussed with reference to FIG. 4.

In still further embodiments, the at least one user-specific electronic recommendation may be rendered in real-time or near-real time during or after the hair is removed. For example, the one or more processors may analyze the at least one image, generate the user-specific electronic recommendation, and render (or cause the user-specific electronic recommendation to be rendered) in real-time after receiving the at least one image. Thus, depending on when the at least one image is captured by the digital camera and received by the one or more processors, the one or more processors may generate and render, in real time, the at least one user-specific electronic recommendation in real-time or near-real time as the hair is removed.

In additional embodiments, a user-specific electronic recommendation may comprise a product recommendation for a manufactured product. In such embodiments, the user-specific electronic recommendation may be displayed on the display screen of a user computing device (e.g., user computing device 111c1) with instructions (e.g., a message) for treating, with the manufactured product, the at least one feature identifiable the pixel data comprising the at least a portion of the user's skin. In still further embodiments, either the user computing device 111c1 and/or imaging server(s) may initiate, based on the product recommendation, a shipment of the manufactured product to the user. Initiating the manufactured product for shipment may include transmitting a message to a manufacturer of the product including information regarding the user (e.g., payment information, mailing information) or notifying a third party that a user may be interested in the manufactured product. Additional details regarding preparing a manufactured product for shipment are discussed with reference to FIG. 4.

Figure 4:
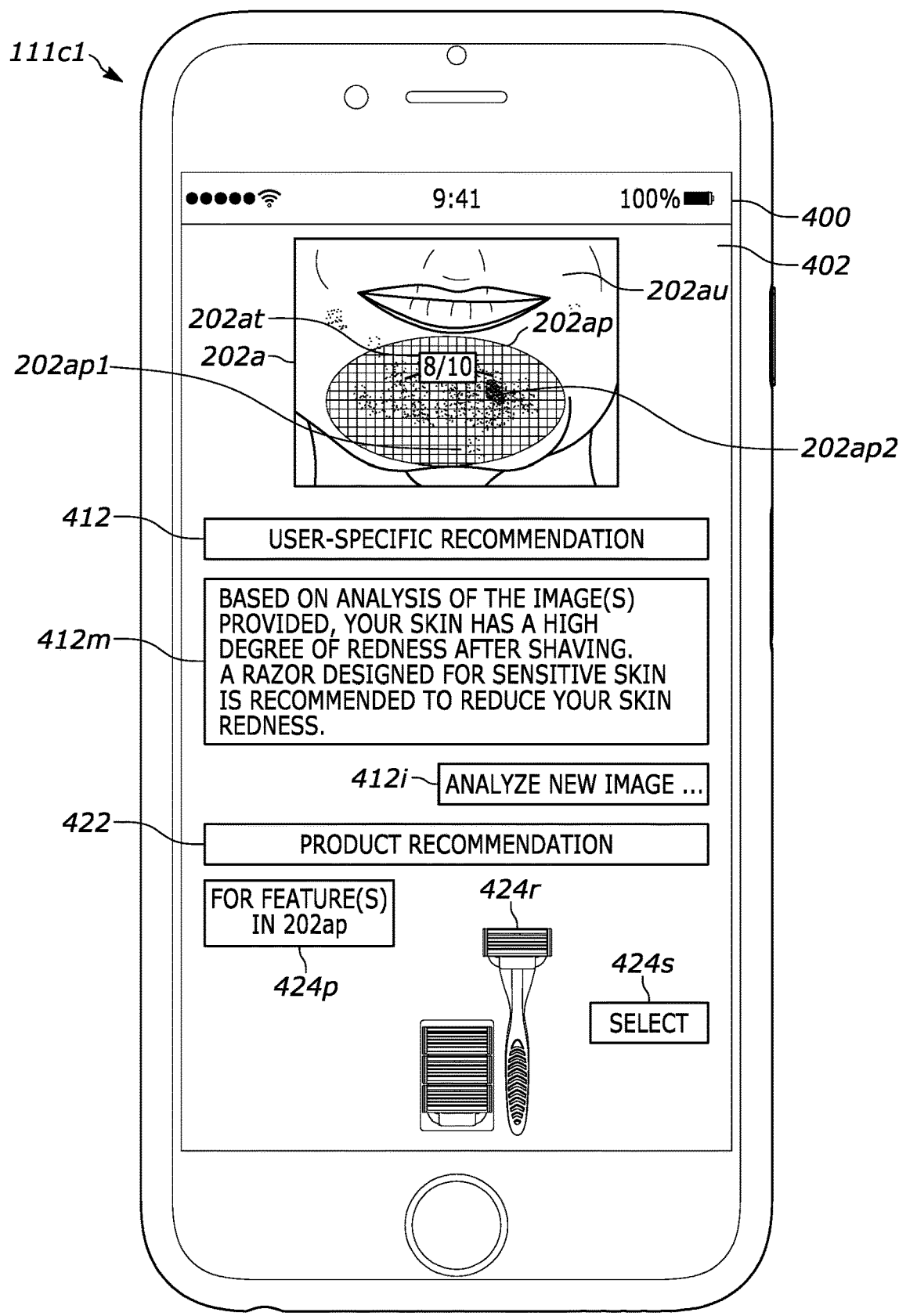
FIG. 4 illustrates an example user interface as rendered on a display screen of a user computing device in accordance with various embodiments disclosed herein.

FIG. 4 illustrates an example user interface 402 as rendered on a display screen 400 of a user computing device 111c1 in accordance with various embodiments disclosed herein. For example, as shown in the example of FIG. 4, user interface 402 may be implemented or rendered via an application (app) executing on user computing device 111c1.

For example, as shown in the example of FIG. 4, user interface 402 may be implemented or rendered via a native app executing on user computing device 111c1. In the example of FIG. 4, user computing device 111c1 is a user computer device as described for FIG. 1, e.g., where 111c1 is illustrated as an APPLE iPhone that implements the APPLE iOS operating system and has display screen 400. User computing device 111c1 may execute one or more native applications (apps) on its operating system. Such native apps may be implemented or coded (e.g., as computing instructions) in a computing language (e.g., SWIFT) executable by the user computing device operating system (e.g., APPLE iOS) by the processor of user computing device 111c1.

Additionally, or alternatively, user interface 402 may be implemented or rendered via a web interface, such as via a web browser application, e.g., Safari and/or Google Chrome app(s), or other such web browser or the like.

As shown in the example of FIG. 4, user interface 402 comprises a graphical representation (e.g., image 202a) of the user's skin. Image 202a may be the at least one image of the user (or graphical representation thereof) after removing hair and as analyzed by the skin redness model (e.g., skin redness model 108) as described herein. In the example of FIG. 4, graphical representation (e.g., image 202a) of the user's skin is annotated with one or more graphics (e.g., area of pixel data 202ap) or textual rendering (e.g., text 202at) corresponding to the user-specific skin redness value. For example, the area of pixel data 202ap may be annotated or overlaid on top of the image of the user (e.g., image 202a) to highlight the area or feature(s) identified within the pixel data (e.g., feature data and/or raw pixel data) by the skin redness model (e.g., skin redness model 108). In the example of FIG. 4, the area of pixel data 202ap and the feature(s) identified within include the user-specific skin redness value of the user's skin after removing hair from the skin, portions of the skin of varying degrees of redness (e.g., areas of little to no redness and areas of high relative redness), and other features shown in area of pixel data 202*ap*. In various embodiments, the pixels identified as the specific features indicating little to no redness (e.g., pixel 202*ap*1 indicating a baseline skin color of user 202*au*) or higher redness (e.g., pixel 202*ap*2 indicating an area of the skin with higher redness than the pixel 202*ap*1) may be highlighted or otherwise annotated when rendered. In some embodiments, a graphical representation depicting how the user's skin is predicted to appear after treating the at least one feature (e.g., an area of skin redness) with a recommended product is may be rendered (e.g., the modified image discussed above).

Textual rendering (e.g., text 202*at*) shows a user-specific skin redness value or other indication of the user-specific skin redness value (e.g., 8/10 on a skin redness scale that is scaled from 0 (least red) to 10 (most red)). The textual rendering may be the user-specific skin redness value output from the skin redness model 108, or may be a qualitative description or scaled version of the user-specific skin redness value. For example, qualitative descriptions may indicate how red the skin is, such as "no redness," "little redness," "moderate redness," or "severe redness." Additionally, or alternatively, color values or patterns may be overlaid on a graphical representation shown on user interface 402 (e.g., image 202*a*) to indicate areas of higher or lower redness.

User interface 402 may also include or render a user-specific electronic recommendation 412. In the embodiment of FIG. 4, user-specific electronic recommendation 412 comprises a message 412*m* to the user designed to address at least one feature identifiable within the pixel data comprising the portion of the user's skin. As shown in the example of FIG. 4, message 412*m* indicates to the user that their skin has a high degree of redness after shaving, and recommends to the user to use a razor designed for sensitive skin to reduce their skin redness. The user-specific electronic recommendation can be made based on the high skin redness value (e.g., 8/10) that the user's skin shows after removing hair, where the razor product is designed to address the issue of skin redness detected in the pixel data of image 202*a* or otherwise assumed based on the high skin redness value. The product recommendation (e.g., the razor recommendation) can be correlated to the identified feature within the pixel data, and the user computing device 111*c*1 and/or imaging server(s) 102 can be instructed to output the product recommendation when the feature (e.g., high skin redness) is identified.

User interface 402 also includes or renders a section for a product recommendation 422 for a manufactured product 424*r* (e.g., a razor designed for sensitive skin, as described above). The product recommendation 422 generally corresponds to the user-specific electronic recommendation 412, as described above. For example, in the example of FIG. 4, the user-specific electronic recommendation 412 is displayed on display screen 400 of user computing device 111*c*1 with instructions (e.g., message 412*m*) for treating, with the manufactured product (manufactured product 424*r* (e.g., a razor designed for sensitive skin) at least one feature (e.g., skin redness at pixel 202*ap*2) identifiable in the pixel data (e.g., pixel data 202*ap*) comprising the at least the portion of the user's skin after hair is removed from the user's skin.

As shown in FIG. 4, user interface 402 recommends a product (e.g., manufactured product 424*r* (e.g., a razor designed for sensitive skin)) based on the user-specific electronic recommendation 412. In the example of FIG. 4, the output or analysis of image(s) (e.g. image 202*a*) of the skin redness model (e.g., skin redness model 108), e.g., user-specific electronic recommendation 412 and/or its related values (e.g., 8/10) or related pixel data (e.g., 202*ap*1 and/or 202*ap*2) may be used to generate or identify recommendations for corresponding product(s). Such recommendations may include products such as pre-hair removal gel or balm, shaving gel, shaving cream, after shave gel or balm, post-hair removal gel or balm, shaving razor, shaving blade (s), a change to a different type of hair removal product, a moisturizing treatment, or the like to address the user-specific issue as detected within the pixel data by the skin redness model (e.g., skin redness model 108).

In the example of FIG. 4, user interface 402 renders or provides a recommended product (e.g., manufactured product 424*r*) as determined by the skin redness model (e.g., skin redness model 108) and its related image analysis of image 202*a* and its pixel data and various features. In the example of FIG. 4, this is indicated and annotated (424*p*) on user interface 402.

User interface 402 may further include a selectable UI button 424*s* to allow a user (e.g., the user of image 202*a*) to select for purchase or shipment the corresponding product (e.g., manufactured product 424*r*). In some embodiments, selection of selectable UI button 424*s* a may cause the recommended product(s) to be shipped to the user (e.g., individual 501) and/or may notify a third party that the individual is interested in the product(s). For example, either user computing device 111*c*1 and/or imaging server(s) 102 may initiate, based on user-specific electronic recommendation 412, the manufactured product 424*r* (e.g., a razor designed for sensitive skin) for shipment to the user. In such embodiments, the product may be packaged and shipped to the user.

In various embodiments, graphical representation (e.g., image 202*a*), with graphical annotations (e.g., area of pixel data 202*ap*), textual annotations (e.g., text 202*at*), user-specific electronic recommendation 412 may be transmitted, via the computer network (e.g., from an imaging server 102 and/or one or more processors) to user computing device 111*c*1, for rendering on display screen 400. In other embodiments, no transmission to the imaging server 102 of the user's specific image occurs, where the user-specific recommendation (and/or product specific recommendation) may instead by generated locally, by the skin redness model (e.g., skin redness model 108) executing and/or implemented on the user's mobile device (e.g., user computing device 111*c*1) and rendered, by a processor of the mobile device, on display screen 300 of the mobile device (e.g., user computing device 111*c*1).

In some embodiments, any one or more of graphical representations (e.g., image 202*a*), with graphical annotations (e.g., area of pixel data 202*ap*), textual annotations (e.g., text 202*at*), user-specific electronic recommendation 412, and/or product recommendation 422 may be rendered (e.g., rendered locally on display screen 400) in real-time or near-real time during or after the user's hair is removed. In embodiments where the image is analyzed by imaging server(s) 102, the image may be transmitted and analyzed in real-time or near real-time by imaging server(s) 102.

In some embodiments the user may provide a new image that may be transmitted to imaging server(s) 102 for updating, retraining, or reanalyzing by skin redness model 108. In other embodiments, a new image that may be locally received on computing device 111*c*1 and analyzed, by skin redness model 108, on the user computing device 111*c*1.

In addition, as shown in the example of FIG. 4, the user may select selectable button 412*i* to for reanalyzing (e.g., either locally at computing device 111c1 or remotely at imaging server(s) 102) a new image. Selectable button 412i may cause user interface 402 to prompt the user to attach for analyzing a new image. Imaging server(s) 102 and/or a user computing device such as user computing device 111c1 may receive a new image of the user after the user removes hair from a portion of the user's skin. The new image may be captured by the digital camera. The new image (e.g., just like image 202a) may comprise pixel data of at least a portion of the user's skin after hair is removed from the at least a portion of the user's skin. The skin redness model (e.g., the skin redness model 108), executing on the memory of the computing device (e.g., imaging server(s) 102 or a user computer device such as the user computer device 111c1), may analyze the new image captured by the digital camera to determine a new user-specific skin redness value being of the user's skin after removing hair. The computing device (e.g., imaging server(s) 102) may generate, based on the new user-specific skin redness value, a new user-specific electronic recommendation or comment regarding at least one feature identifiable within the pixel data of the new image. The new user-specific electronic recommendation may be based on a comparison of the new user-specific skin redness value and the initial or previous user-specific skin redness value. For example, the computing device (e.g., imaging server(s) 102) may generate a delta skin redness value based on a comparison between the new user-specific skin redness value and the initial or previous user-specific skin redness value (e.g., the delta skin redness value may correspond to a previously determined user-specific skin redness value minus the new user-specific skin redness value. In some examples, the new user-specific electronic recommendation or comment may include a comparative comment based on a comparison between the new user-specific skin redness value and the initial or previous user-specific skin redness value (e.g., the comparative comment may indicate whether the user improved their skin redness).

The new user-specific electronic recommendation may include a new graphical representation including graphics and/or text (e.g., showing a new user-specific skin redness value, e.g., 6/10, showing a delta skin redness value, and/or showing the comparative comment). In some examples, the at least one image and the new image may be rendered on the display screen of the user computing device such that the user may compare the images. The new user-specific electronic recommendation may include additional recommendations (e.g., that the user has reduced their skin redness value but that there are ways to further improve their skin redness value) as detected with the pixel data of the new image. A comment may include that the user has corrected the at least one feature identifiable within the pixel data comprising the at least the portion of the user's skin (e.g., the skin redness value is now close to 0/10, where 0 indicates baseline skin color). In some embodiments, the new user-specific recommendation or comment may be transmitted via the computer network to the user computing device of the user for rendering on the display screen of the user computing device. In other embodiments, no transmission to the imaging server of the user's new image occurs, where the new user-specific recommendation (and/or product specific recommendation) may instead be generated locally, by the skin redness model (e.g., skin redness model 108) executing and/or implemented on the user's mobile device (e.g., user computing device 111c1) and rendered, by a processor of the mobile device, on a display screen of the mobile device (e.g., user computing device 111c1).

ASPECTS OF THE DISCLOSURE

The following aspects are provided as examples in accordance with the disclosure herein and are not intended to limit the scope of the disclosure.

1. A digital imaging method of analyzing pixel data of an image of a user's body for determining a user-specific skin redness value of the user's skin after removing hair, the digital imaging method comprising the steps of: a. aggregating, at one or more processors communicatively coupled to one or more memories, a plurality of training images of a plurality of individuals, each of the training images comprising pixel data of skin of a respective individual after removing hair; b. training, by the one or more processors with the pixel data of the plurality of training images, a skin redness model comprising a skin redness scale and operable to output, across a range of the skin redness scale, skin redness values associated with a degree of skin redness ranging from least red to most red; c. receiving, at the one or more processors, at least one image of a user, the at least one image captured by a digital camera, and the at least one image comprising pixel data of at least a portion of the user's skin after hair is removed from the at least a portion of the user's skin; d. analyzing, by the skin redness model executing on the one or more processors, the at least one image captured by the digital camera to determine a user-specific skin redness value of the user's skin; e. generating, by the one or more processors based on the user-specific skin redness value, at least one user-specific electronic recommendation designed to address at least one feature identifiable within the pixel data of the at least a portion of the user's skin; and f. rendering, on a display screen of a user computing device, the at least one user-specific electronic recommendation.

2. The digital imaging method of aspect 1, wherein the at least one user-specific electronic recommendation is displayed on the display screen of the user computing device with a graphical representation of the user's skin as annotated with one or more graphics or textual renderings corresponding to the user-specific skin redness value.

3. The digital imaging method of any one of aspects 1-2, wherein the at least one user-specific electronic recommendation comprises a product recommendation for a manufactured product.

4. The digital imaging method of aspect 3, wherein the at least one user-specific electronic recommendation is displayed on the display screen of the user computing device with instructions for treating, with the manufactured product, the at least one feature.

5. The digital imaging method of aspect 4, further comprising: generating, by the one or more processors, a modified image based on the at least one image, the modified image depicting how the user's skin is predicted to appear after treating the at least one feature with the manufactured product; and rendering, on the display screen of the user computing device, the modified image.

6. The digital imaging method of any one of aspects 3-5, further comprising the steps of: initiating, based on the product recommendation, a shipment of the manufactured product to the user.

7. The digital imaging method of any one of aspects 1-6, wherein the at least one user-specific electronic recommendation includes a behavior recommended based on the user-specific skin redness value.

8. The digital imaging method of any one of aspects 1-7, wherein the skin redness model is an artificial intelligence (AI) based model trained with at least one AI algorithm.

9. The digital imaging method of any one of aspects 1-8, wherein the skin redness model is further trained, by the one or more processors with the pixel data of the plurality of training images, to output one or more body area locations of respective individuals, and wherein the skin redness model, executing on the one or more processors and analyzing the at least one image of the user, determines a location identifier indicating a body area location of the user's body or body area.

10. The digital imaging method of aspect 9, wherein the body area location comprises at least one of the user's face, the user's cheek, the user's neck, the user's jaw, the user's head, the user's groin, the user's underarm, the user's chest, the user's back, the user's leg, the user's arm, or the user's bikini area.

11. The digital imaging method of any one of aspects 1-10, wherein the hair is removed from the at least a portion of the user's skin by a wet razor, a dry shaver, an epilator, a light based hair removal device, a depilatory cream, or a wax.

12. The digital imaging method of any one of aspects 1-11, wherein the at least one image is captured by the digital camera within one hour after the hair is removed.

13. The digital imaging method of any one of aspects 1-12, wherein training, by the one or more processors with the pixel data of the plurality of training images, the skin redness model comprises training the skin redness model to determine color values of pixels included in the pixel data of the at least a portion of the user's skin to determine the user-specific skin redness value.

14. The digital imaging method of any one of aspects 1-13, further comprising: receiving, at the one or more processors, a new image of the user, the new image captured by the digital camera, and the new image comprising new pixel data of at least a portion of the user's skin after hair is removed from the at least a portion of the user's skin; analyzing, by the skin redness model executing on the one or more processors, the new image captured by the digital camera to determine a new user-specific skin redness value; generating, based on the new user-specific skin redness value, a new user-specific electronic recommendation or comment regarding at least one new feature identifiable within the new pixel data of the new image; and rendering, on the display screen of the user computing device, the new user-specific electronic recommendation or comment.

15. The digital imaging method of aspect 14, wherein a delta skin redness value is generated based on a comparison between the new user-specific skin redness value and the user-specific skin redness value, and wherein the new user-specific electronic recommendation or comment is further based on the delta skin redness value.

16. The digital imaging method of any one of aspects 14-15, wherein the new user-specific recommendation or comment includes a comparative comment based on a comparison between the new user-specific skin redness value and the user-specific skin redness value.

17. The digital imaging method of any one of aspects 1-16, wherein the one or more processors comprises at least one of a server or a cloud-based computing platform, and the server or the cloud-based computing platform receives the plurality of training images of the plurality of individuals via a computer network, and wherein the server or the cloud-based computing platform trains the skin redness model with the pixel data of the plurality of training images.

18. The digital method of aspect 17, wherein the server or the cloud-based computing platform receives the at least one image comprising the pixel data of the at least a portion of the user's skin, and wherein the server or the cloud-based computing platform executes the skin redness model and generates, based on output of the skin redness model, the user-specific electronic recommendation and transmits, via the computer network, the user-specific electronic recommendation to the user computing device for rendering on the display screen of the user computing device.

19. The digital imaging method of any one of aspects 1-18, wherein the user computing device comprises at least one of a mobile device, a tablet, a handheld device, a desktop device, a home assistant device, a personal assistant device, or a retail computing device.

20. The digital imaging method of any one of aspects 1-17 or 19, wherein the user computing device receives the at least one image comprising the pixel data of the at least a portion of the user's skin, and wherein the user computing device executes the skin redness model and generates, based on the output of the skin redness model, the user-specific electronic recommendation, and renders the user-specific recommendation on the display screen of the user computing device.

21. The digital imaging method of any one of aspects 1-20, wherein the at least one image comprises a plurality of images.

22. The digital imaging method of aspect 21, wherein the plurality of images are collected using a digital video camera.

23. The digital imaging method of any one of aspects 1-22, wherein the at least one user-specific electronic recommendation is rendered in real-time or near-real time during or after the hair is removed.

24. A digital imaging system configured to analyze pixel data of an image of a user's body for determining a skin redness value of the user's skin after removing hair, the digital imaging system comprising: an imaging server comprising a server processor and a server memory; an imaging application (app) configured to execute on a user computing device comprising a device processor and a device memory, the imaging app communicatively coupled to the imaging server; and a skin redness model comprising a skin redness scale, the skin redness model trained with pixel data of a plurality of training images of individuals and operable to determine, across a range of the skin redness scale, skin redness values associated with a degree of skin redness ranging from least red to most red; wherein the skin redness model is configured to execute on the server processor or the device processor to cause the server processor or the device processor to: receive at least one image of a user, the at least one image captured by a digital camera, and the at least one image comprising pixel data of at least a portion of the user's skin after hair is removed from the at least a portion of the user's skin, analyze, by the skin redness model, the at least one image captured by the digital camera to determine a user-specific skin redness value of the user's skin, generate, based on the user-specific skin redness value, at least one user-specific electronic recommendation designed to address at least one feature identifiable within the pixel data comprising the at least a portion of the user's skin; and render, on a display screen of the user computing device of the user, the at least one user-specific electronic recommendation.

25. A tangible, non-transitory computer-readable medium storing instructions for analyzing pixel data of an image of a user's body for determining a skin redness value of the user's skin after removing hair, that when executed by one or more processors, cause the one or more processors to: a. aggregate, at one or more processors communicatively coupled to one or more memories, a plurality of training images from a plurality of individuals, each of the training images comprising pixel data of skin of a respective individual after removing hair; b. train, by the one or more processors with the pixel data of the plurality of training images, a skin redness model comprising a skin redness scale and operable to output, across a range of the skin redness scale, skin redness values associated with a degree of skin redness ranging from least red to most red; c. receive, at the one or more processors, at least one image of a user, the at least one image captured by a digital camera, and the at least one image comprising pixel data of at least a portion of the user's skin after hair is removed from the at least a portion of the user's skin; d. analyze, by the skin redness model executing on the one or more processors, the at least one image captured by the digital camera to determine a user-specific skin redness value of the user's skin; e. generate, by the one or more processors based on the user-specific skin redness value, at least one user-specific electronic recommendation designed to address at least one feature identifiable within the pixel data of the at least a portion of the user's skin; and f. render, on a display screen of a user computing device, the at least one user-specific electronic recommendation.

Additional Considerations

Although the disclosure herein sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

This detailed description is to be construed as exemplary only and does not describe every possible embodiment, as describing every possible embodiment would be impractical, if not impossible. A person of ordinary skill in the art may implement numerous alternate embodiments, using either current technology or technology developed after the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited.

The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A digital imaging method of analyzing pixel data of an image of a user's body for determining a user-specific skin redness value of the user's skin after removing hair, the digital imaging method comprising the steps of:
    a. aggregating, at one or more processors communicatively coupled to one or more memories, a plurality of training images of a plurality of individuals, each of the training images comprising pixel data of skin of a respective individual after removing hair;
    b. training, by the one or more processors with the pixel data of the plurality of training images, a skin redness model comprising a skin redness scale and operable to output, across a range of the skin redness scale, skin redness values associated with a degree of skin redness ranging from least red to most red;
    c. receiving, at the one or more processors, at least one image of a user, the at least one image captured by a digital camera, and the at least one image comprising pixel data of at least a portion of the user's skin after hair is removed from the at least a portion of the user's skin;
    d. analyzing, by the skin redness model executing on the one or more processors, the at least one image captured by the digital camera to determine a user-specific skin redness value of the user's skin;
    e. generating, by the one or more processors based on the user-specific skin redness value, at least one user-specific electronic recommendation designed to address at least one feature identifiable within the pixel data of the at least a portion of the user's skin; and
    f. rendering, on a display screen of a user computing device, the at least one user-specific electronic recommendation.

2. The digital imaging method of claim 1, wherein the at least one user-specific electronic recommendation is displayed on the display screen of the user computing device with a graphical representation of the user's skin as annotated with one or more graphics or textual renderings corresponding to the user-specific skin redness value.

3. The digital imaging method of claim 1, wherein the at least one user-specific electronic recommendation comprises a product recommendation for a manufactured product.

4. The digital imaging method of claim 3, wherein the at least one user-specific electronic recommendation is displayed on the display screen of the user computing device with instructions for treating, with the manufactured product, the at least one feature.

5. The digital imaging method of claim 4, further comprising: generating, by the one or more processors, a modified image based on the at least one image, the modified image depicting how the user's skin is predicted to appear after treating the at least one feature with the manufactured product; and rendering, on the display screen of the user computing device, the modified image.

6. The digital imaging method of claim 3, further comprising the steps of:
    initiating, based on the product recommendation, a shipment of the manufactured product to the user.

7. The digital imaging method of claim 1, wherein the at least one user-specific electronic recommendation includes a behavior recommended based on the user-specific skin redness value.

8. The digital imaging method of claim 1, wherein the skin redness model is an artificial intelligence (AI) based model trained with at least one AI algorithm.

9. The digital imaging method of claim 1,
    wherein the skin redness model is further trained, by the one or more processors with the pixel data of the plurality of training images, to output one or more body area locations of respective individuals, and
    wherein the skin redness model, executing on the one or more processors and analyzing the at least one image of the user, determines a location identifier indicating a body area location of the user's body or body area.

10. The digital imaging method of claim 9, wherein the body area location comprises at least one of the user's face, the user's cheek, the user's neck, the user's jaw, the user's head, the user's groin, the user's underarm, the user's chest, the user's back, the user's leg, the user's arm, or the user's bikini area.

11. The digital imaging method of claim 1, wherein the hair is removed from the at least a portion of the user's skin by a wet razor, a dry shaver, an epilator, a light based hair removal device, a depilatory cream, or a wax.

12. The digital imaging method of claim 1, wherein the at least one image is captured by the digital camera within one hour after the hair is removed.

13. The digital imaging method of claim 1, wherein training, by the one or more processors with the pixel data of the plurality of training images, the skin redness model comprises training the skin redness model to determine color values of pixels included in the pixel data of the at least a portion of the user's skin to determine the user-specific skin redness value.

14. The digital imaging method of claim 1, further comprising:
    receiving, at the one or more processors, a new image of the user, the new image captured by the digital camera, and the new image comprising new pixel data of at least a portion of the user's skin after hair is removed from the at least a portion of the user's skin;
    analyzing, by the skin redness model executing on the one or more processors, the new image captured by the digital camera to determine a new user-specific skin redness value;
    generating, based on the new user-specific skin redness value, a new user-specific electronic recommendation or comment regarding at least one new feature identifiable within the new pixel data of the new image; and
    rendering, on the display screen of the user computing device, the new user-specific electronic recommendation or comment.

15. The digital imaging method of claim 14, wherein a delta skin redness value is generated based on a comparison between the new user-specific skin redness value and the user-specific skin redness value, and wherein the new user-specific electronic recommendation or comment is further based on the delta skin redness value.

16. The digital imaging method of claim 14, wherein the new user-specific recommendation or comment includes a comparative comment based on a comparison between the new user-specific skin redness value and the user-specific skin redness value.

17. The digital imaging method of claim 1, wherein the one or more processors comprises at least one of a server or a cloud-based computing platform, and the server or the cloud-based computing platform receives the plurality of training images of the plurality of individuals via a computer network, and wherein the server or the cloud-based computing platform trains the skin redness model with the pixel data of the plurality of training images.

18. The digital method of claim 17, wherein the server or the cloud-based computing platform receives the at least one image comprising the pixel data of the at least a portion of the user's skin, and wherein the server or the cloud-based computing platform executes the skin redness model and generates, based on output of the skin redness model, the user-specific electronic recommendation and transmits, via the computer network, the user-specific electronic recommendation to the user computing device for rendering on the display screen of the user computing device.

19. The digital imaging method of claim 1, wherein the user computing device comprises at least one of a mobile device, a tablet, a handheld device, a desktop device, a home assistant device, a personal assistant device, or a retail computing device.

20. The digital imaging method of claim 1, wherein the user computing device receives the at least one image comprising the pixel data of the at least a portion of the user's skin, and wherein the user computing device executes the skin redness model and generates, based on the output of the skin redness model, the user-specific electronic recommendation, and renders the user-specific recommendation on the display screen of the user computing device.

21. The digital imaging method of claim 1, wherein the at least one image comprises a plurality of images.

22. The digital imaging method of claim 21, wherein the plurality of images are collected using a digital video camera.

23. The digital imaging method of claim 1, wherein the at least one user-specific electronic recommendation is rendered in real-time or near-real time during or after the hair is removed.

24. A digital imaging system configured to analyze pixel data of an image of a user's body for determining a skin redness value of the user's skin after removing hair, the digital imaging system comprising:
   an imaging server comprising a server processor and a server memory;
   an imaging application (app) configured to execute on a user computing device comprising a device processor and a device memory, the imaging app communicatively coupled to the imaging server; and
   a skin redness model comprising a skin redness scale, the skin redness model trained with pixel data of a plurality of training images of individuals and operable to determine, across a range of the skin redness scale, skin redness values associated with a degree of skin redness ranging from least red to most red;
   wherein the skin redness model is configured to execute on the server processor or the device processor to cause the server processor or the device processor to:
      receive at least one image of a user, the at least one image captured by a digital camera, and the at least one image comprising pixel data of at least a portion of the user's skin after hair is removed from the at least a portion of the user's skin,
      analyze, by the skin redness model, the at least one image captured by the digital camera to determine a user-specific skin redness value of the user's skin,
      generate, based on the user-specific skin redness value, at least one user-specific electronic recommendation designed to address at least one feature identifiable within the pixel data comprising the at least a portion of the user's skin; and
      render, on a display screen of the user computing device of the user, the at least one user-specific electronic recommendation.

25. A tangible, non-transitory computer-readable medium storing instructions for analyzing pixel data of an image of a user's body for determining a skin redness value of the user's skin after removing hair, that when executed by one or more processors, cause the one or more processors to:
   a. aggregate, at one or more processors communicatively coupled to one or more memories, a plurality of training images from a plurality of individuals, each of the training images comprising pixel data of skin of a respective individual after removing hair;
   b. train, by the one or more processors with the pixel data of the plurality of training images, a skin redness model comprising a skin redness scale and operable to output, across a range of the skin redness scale, skin redness values associated with a degree of skin redness ranging from least red to most red;
   c. receive, at the one or more processors, at least one image of a user, the at least one image captured by a digital camera, and the at least one image comprising pixel data of at least a portion of the user's skin after hair is removed from the at least a portion of the user's skin;
   d. analyze, by the skin redness model executing on the one or more processors, the at least one image captured by the digital camera to determine a user-specific skin redness value of the user's skin;
   e. generate, by the one or more processors based on the user-specific skin redness value, at least one user-specific electronic recommendation designed to address at least one feature identifiable within the pixel data of the at least a portion of the user's skin; and
   f. render, on a display screen of a user computing device, the at least one user-specific electronic recommendation.

* * * * *